United States Patent
Zaleski

(10) Patent No.: US 11,246,542 B2
(45) Date of Patent: Feb. 15, 2022

(54) METHOD FOR ADJUSTING AN ALARM BASED ON THE PRECEDING QUANTITY OF THRESHOLD BREACHES

(71) Applicant: PHILIPS CAPSULE CORPORATION, Cambridge, MA (US)

(72) Inventor: John Zaleski, Elkton, MD (US)

(73) Assignee: PHILIPS CAPSULE CORPORATION, Cambridge, MA (US)

( * ) Notice: Subject to any disclaimer, the term of this patent is extended or adjusted under 35 U.S.C. 154(b) by 174 days.

(21) Appl. No.: 16/363,053

(22) Filed: Mar. 25, 2019

(65) Prior Publication Data

US 2019/0290218 A1 Sep. 26, 2019

Related U.S. Application Data

(60) Provisional application No. 62/647,991, filed on Mar. 26, 2018.

(51) Int. Cl.

| A61B 5/1455 | (2006.01) |
|---|---|
| A61B 5/00 | (2006.01) |
| A61B 5/026 | (2006.01) |
| A61B 5/021 | (2006.01) |
| A61B 5/08 | (2006.01) |
| A61B 5/024 | (2006.01) |

(52) U.S. Cl.
CPC .......... *A61B 5/746* (2013.01); *A61B 5/14551* (2013.01); *A61B 5/021* (2013.01); *A61B 5/024* (2013.01); *A61B 5/026* (2013.01); *A61B 5/0816* (2013.01)

(58) Field of Classification Search
CPC ..... A61B 5/14551; A61B 5/746; A61B 5/021; A61B 5/024; A61B 5/026; A61B 5/0816; A61B 5/72; A61B 6/7235; A61B 5/7242; A61B 5/1455; A61B 5/14552; A61B 5/14532; A61B 5/0205; A61B 5/7235
See application file for complete search history.

(56) References Cited

U.S. PATENT DOCUMENTS

| 5,865,736 A | * | 2/1999 | Baker, Jr. | ............. | A61B 5/1455 600/323 |
| 6,754,516 B2 | * | 6/2004 | Mannheimer | ...... | A61B 5/14551 600/309 |

(Continued)

*Primary Examiner* — Chu Chuan Liu

(57) ABSTRACT

A method and system for adjusting the AUC limit threshold to reduce the number of false alarms. In one embodiment the method includes the steps of: defining a AUC limit threshold; defining a saturation limit threshold for a desired oxygen saturation level; periodically measuring a patient's measured oxygen saturation level over time; calculating the difference between the patient's measured oxygen saturation and defined saturation limit threshold; summing the differences between the patient's measured oxygen saturation and defined saturation limit threshold over a time interval wherein the patient's measured oxygen saturation is less than defined saturation limit threshold, wherein the summation defines a measured AUC; comparing the measured AUC over the time interval against the defined AUC limit threshold; determining regions in which the measured AUC exceeds the defined AUC limit threshold; and adjusting the AUC limit threshold.

8 Claims, 9 Drawing Sheets

(56) References Cited

U.S. PATENT DOCUMENTS

| | | | |
|---|---|---|---|
| 8,852,115 B2* | 10/2014 | Muir | A61B 5/746 600/500 |
| 2010/0075353 A1* | 3/2010 | Heaton | A61B 5/14551 600/324 |
| 2013/0204105 A1* | 8/2013 | Benni | G16H 40/63 600/323 |
| 2015/0051463 A1* | 2/2015 | Curtis | A61B 5/02416 600/324 |
| 2017/0164832 A1* | 6/2017 | Kaib | A61B 5/6805 |

* cited by examiner

METHOD FOR ADJUSTING AN ALARM BASED ON THE PRECEDING QUANTITY OF THRESHOLD BREACHES

CROSS REFERENCE TO RELATED APPLICATIONS

This application claims priority to and benefit of U.S. Provisional Application No. 62/647,991 filed on Mar. 26, 2018, the entire disclosure of which is incorporated by reference herein.

FIELD OF TECHNOLOGY

The invention relates generally to a method of adjusting the threshold for saturation $O_2$ breaches and more specifically to adjusting an alarm threshold based on the quantity of such threshold breaches.

BACKGROUND

Many documentation and monitoring systems in acute care settings of healthcare enterprises employ a user interface for documenting clinical information such as patient vital signs, infusions, outputs such as blood and urine flow, laboratory values, notes, images, and orders. Some of these documentation and monitoring systems include alarm systems to notify clinicians of a patient's health status and breaches of predetermined thresholds for various patient parameters. Some alarm systems allow clinicians to set alarm threshold values and record subsequent alarm system events.

During hospitalization, one of the monitored parameters is a patient's blood oxygen saturation, $Sat_{O_2}$, level. This oxygen saturation level is monitored to detect insufficient $O_2$ perfusion or hypoxemia. Healthcare professionals may set threshold saturation values in various patient monitoring devices to sound an alarm when a patient's blood oxygen saturation level drops to a dangerous level.

Alarm systems in clinical settings are often static in that they: (1) do not permit dynamic manipulation of alarm thresholds in real-time; (2) are limited in that they require alarm thresholds to be set by clinicians; (3) are not capable of being changed remotely; (4) do not have analysis tools to determine alarm thresholds in real time; (5) do not provide an easy and simple way to toggle between alarm thresholds; and (6) do not provide the capability to alter or manipulate alarm thresholds based on the frequency of alarms. This lack of flexibility frequently results is alarms being issued that are unnecessary, causing interruption of the care of other patients.

What is needed is a method to adjust the alarm threshold values in response to the frequency of alarm system events with the intent of reducing unnecessary alarms but without exposing the patient to increased risk of not detecting a significant event. The present invention addresses this need.

SUMMARY

In one aspect, the present application is directed to identify whether certain patients whose vital signs are being monitored continuously, should be reviewed more frequently or less frequently than others based on the time-series history of the SatO2 and the number of threshold breaches experienced within a given time window.

BRIEF DESCRIPTION OF DRAWINGS

Various features of the embodiments described herein, together with advantages thereof, may be understood in accordance with the following description taken in conjunction with the accompanying drawings in which.

DETAILED DESCRIPTION

Figure 1:
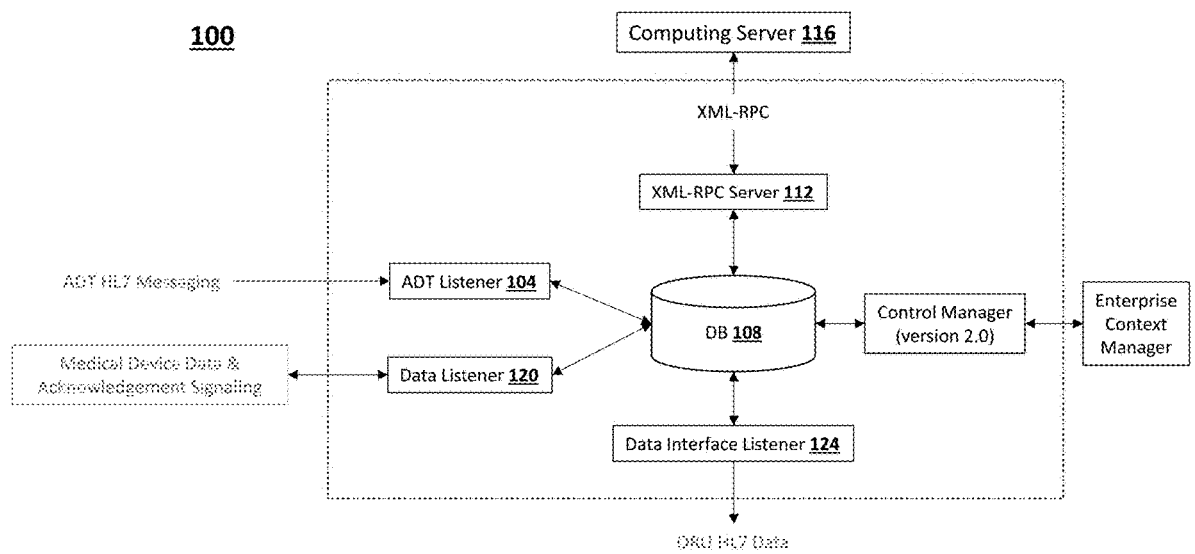
FIG. 1 is a block diagram of the system implementing the method of the invention.

In the following detailed description, reference is made to the accompanying drawings, which are herein included as a portion of the present disclosure. In the drawings, similar symbols and reference characters typically identify similar components throughout the several views, unless context dictates otherwise. The illustrative aspects described in the detailed description, drawings, and claims are not meant to be limiting. Other aspects may be utilized, and other changes may be made, without departing from the scope of the subject matter presented in the present disclosure.

The present invention is a significant improvement of a known method for adjusting the saturation limit threshold for generating an alarm known as SatSeconds™ (Medtronic, Dublin, Ireland). The method of the present invention is termed an area-under-curve $SatO_2$ calculation, hereinafter "$SatO_2$ AUC", or simply "AUC". This improved method of adjusting the threshold is based in part on the preceding total quantity of patient saturation limit threshold breaches. The objective of this improvement is to provide a customized or personalized $SatO_2$ AUC threshold alarm that is unique to each patient, which can be adjusted to avoid unnecessary alarms and which can be monitored remotely.

FIG. 1 is a block diagram of an alarm system for implementing the described method. In one embodiment the system 100 includes an ADT Listener 104 configured to receive patient demographic traffic and populate a database 108, and an XML-RPC Server 112 (as determined by a particular embodiment of the system architecture) configured to communicate data to a user-interface on a server or other computer 116 and to generate notifications sent to a user based on the threshold(s) and/or user defined rules. The system also includes a data listener 120 configured to communicate with a system for medical device traffic, and a data server 124 configured to communicate validated data measurements to outbound Health Level 7 (HL7) Interface Engine. In one embodiment the interface engine is a VEGA System HL7 Interface Engine (Bernoulli Enterprise, Inc, Milford, Conn. 06460).

In some embodiments, XML-RPC Server 112 includes a notification tool configured to send a notification to the user when a parameter satisfies a user-defined rule and/or exceeds a threshold value. In various embodiments, computing device 116 can be used any computing device, e.g., a smartphone, tablet PC, laptop computers, etc., configured to display user-interfaces described herein. It should be understood by those of ordinary skill in the art that XML-RPC server 112 and computing device 116 are only examples and that other types of servers and computing devices are further contemplated according to aspects of the present invention. In various embodiments, multiple types of physiologic monitors systems communicate through an HL7 gateway, and traffic is differentiated by patient specific identifiers and location.

Figure 2:
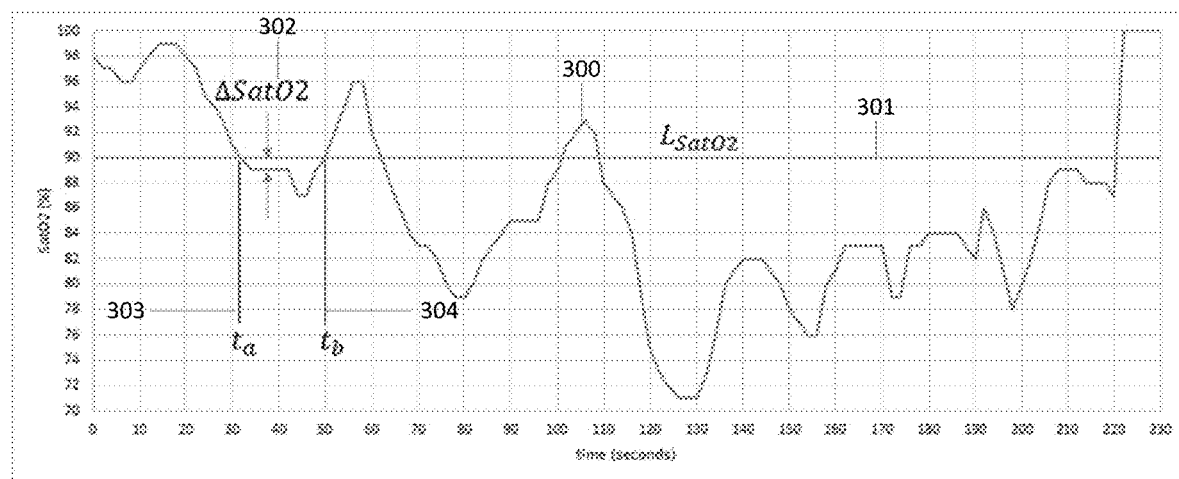
FIG. 2 is a time-series plot of oxygen saturation versus time showing the principal mathematical components of the method.
Figure 3:
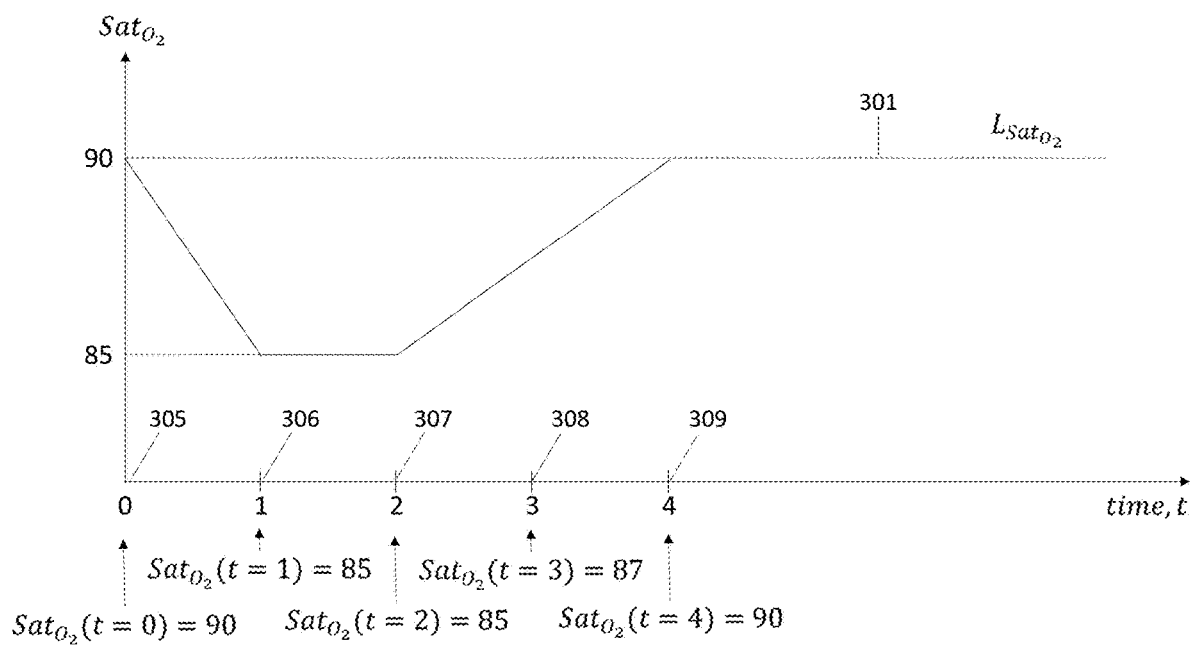
FIG. 3 is an exemplary diagram of the area-under-curve (AUC) calculation methodology.

To facilitate understanding of the calculation, FIG. 2 and FIG. 3 are referenced for discussion. In FIG. 2, the oxygen saturation of a patient, as periodically measured by an oximeter, is shown. The graph depicts the arterial oxygen saturation percent ($Sat_{O_2}$) (y-axis) in the blood of a patient displayed versus time (x-axis) 300. A limit threshold, $L_{SatO2}$, 301 identifying a percentage of oxygen saturation ($Sat_{O_2}$) below which there is a cautionary or emergent concern for the patient's oxygen perfusion is also shown. In one embodiment the level oxygen saturation below which there is concern is 90%. Oxygen saturation below this level typically would cause an alarm to be issued.

A key metric in an embodiment of the area-under-curve (AUC) method of setting alarm is the period of time during which the oxygen saturation measurements 300, obtained from a patient, drop consecutively below the limit threshold $$L_{Sat_{O_2}}.$$

The instantaneous difference between the measurement of the oxygen saturation ($Sat_{O_2}$) 300 at a given time (t) and the value of the set threshold $$L_{Sat_{O_2}}$$

is termed the residual or $Sat_{O_2}$ 302. The time interval that is to be used in the AUC measurement is that time period during which the $Sat_{O_2}$ measurements drop below the limit threshold $$L_{Sat_{O_2}}.$$

In this example this interval is between times $t_a$ 303 and $t_b$ 304, respectively.

To calculate the AUC, oxygen saturation levels are analyzed as shown in equations (1 and 2) below. Specifically, the residual or the deviation $\Delta Sat_{O_2}$ of the measured oxygen saturation percentage ($Sat_{O_2}(t)$) at a given time (t) from the threshold level ($L_{Sat_{O_2}}$) is given by:

$$\Delta Sat_{O_2} = (L_{Sat_{O_2}} - Sat_{O_2}(t)) \qquad \text{Equation (1)}$$

The AUC calculation is actually the integral of the residuals from one time step to the next wherein the residual ($\Delta Sat_{O_2}$) is determined to be greater than zero.

$$AUC(t_a, t_b) = \int_{t_a}^{t_b} \Delta Sat_{O_2} dt \qquad \text{s.t. } \forall \Delta Sat_{O_2} \geq 0^1 \qquad \text{Equation (2)}$$

In this case the AUC is over the interval ($t_a$, $t_b$).

[1]Note: s.t.→such that; $\forall \Delta Sat_{O_2} \geq 0$→"for all delta SatO2 greater-than-or-equal-to zero Because a mathematical equation of measured oxygen saturation curve is generally not known, an approximation of the area between the measured curve and the threshold level is used by summing a series of areas that approximate the AUC.

$$AUC(t_a, t_b) = \sum_{t_a}^{t_b} \Delta Sat_{O_2} \Delta t \qquad \text{Equation (3)}$$

Referring to FIG. 3, an example of the AUC approximation over the time interval from 0 to 4 is depicted. The x-axis intervals are units of seconds of time. The calculation of AUC involves computing the residual $\Delta Sat_{O_2}(t)$ at each time interval and summing the areas between any two time intervals, $\Delta t$. The two values of $\Delta Sat_{O_2}(t)$ at the beginning and end of each time interval form a rudimentary trapezoid. Note that discrete integration can typically approximate the shape of the segments using rectangles or trapezoids. For small segments, the trapezoid approximates a rectangle and can take into account slight differences in the shape of the signal from time step to time step. The integration involves computing the areas of each trapezoid and summing them. For the example shown in FIG. 3, the individual residuals are computed as follows in Equation (4a-e), which is an enumeration of Equation (1) for the specific example under consideration:

(a) $\Delta Sat_{O_2}(t=0)=90-90=0$ (b) $\Delta Sat_{O_2}(t=1)=90-85=5$ (c) $\Delta Sat_{O_2}(t=2)=90-85=5$ (d) $\Delta Sat_{O_2}(t=3)=90-87=3$     Equation (4a-e)

(e) $\Delta Sat_{O_2}(t=4)=90-90=0$

The AUC calculation then follows by employing the trapezoidal rule to the discrete integration of each residual over the time interval from 0 to 4 305, 306, 307, 308, 309 in increments of 1. That is, $\Delta t=1$.

$$AUC(t=0, t=4) = \qquad \text{Equation (5)}$$
$$\frac{[\Delta Sat_{O_2}(t=0) + \Delta Sat_{O_2}(t=1)]}{2} \times (1-0) +$$
$$\frac{[\Delta Sat_{O_2}(t=1) + \Delta Sat_{O_2}(t=2)]}{2} \times (2-1) +$$
$$\frac{[\Delta Sat_{O_2}(t=2) + \Delta Sat_{O_2}(t=3)]}{2} \times (3-2) +$$
$$\frac{[\Delta Sat_{O_2}(t=4) + \Delta Sat_{O_2}(t=3)]}{2} \times (4-3)$$

Substituting the values:

$$AUC(t=0, t=4) = \qquad \text{Equation (6)}$$
$$\frac{[0+5]}{2} \times (1) + \frac{[5+5]}{2} \times (1) + \frac{[5+3]}{2} \times (1) + \frac{[3+0]}{2} \times (1)$$

$$AUC(t=0, t=4) = 2.5 + 5 + 4 + 1.5 = 13 \qquad \text{Equation (7)}$$

The AUC value is 13 in this simple example.

Figure 4:
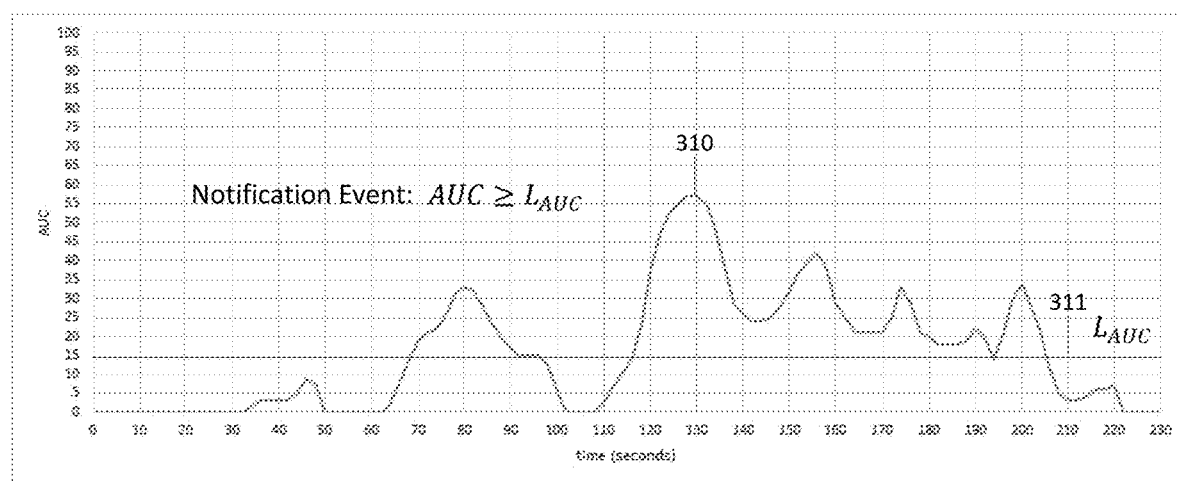
FIG. 4 is a graph depicting the AUC versus time and showing an example AUC threshold $L_{AUC}$.

If the AUC calculation is applied to the saturation curve of FIG. 2, the result is shown in FIG. 4. FIG. 4 is a graph of the AUC plotted against time 310. In this graph a threshold AUC ($L_{AUC}$) 311 is drawn indicating a threshold that will indicate when the AUC 310 has exceeded the predetermined limit ($L_{AUC}$) 311. Note this is similar to FIG. 2 which plots oxygen saturation versus time and indicates when the oxygen saturation is below a specified lower threshold. Both diagrams signify different ways to indicate when the patient's oxygen saturation is below a limit that should cause concern. The AUC threshold ($L_{AUC}$) 311 may be set using various criteria. This threshold may be set according to the clinician's experience, experience regarding a given medical unit, experience regarding a given patient demographic or it may be set in response to the patient's historical value of AUC.

An empirical observation from the patient sample is that there is a relationship between the number of $Sat_{O_2}$ limit threshold breaches (or crossings[2]), the value of the limit threshold of $Sat_{O_2}$, and the AUC value. For example, from FIG. 8, for a specific $Sat_{O_2}$ limit threshold (say, 85%), the number of limit threshold breaches (or crossings) correlates highly with the AUC above a value of 25 (i.e., limit threshold crossings correlate with the AUC>25 with a correlation of 92%). This correlation reduces slightly to 90% with the AUC at 30 or more, and then begins to drop off sharply thereafter.

[2] A $Sat_{O_2}$ limit threshold crossing occurs when a measurement of $Sat_{O_2}$ drops below the identified limit threshold established for the parameter $Sat_{O_2}$. For instance, if the limit threshold is 85% and an individual measurement is 82%, this corresponds to a limit threshold crossing.

Similarly, for a $Sat_{O_2}$ limit threshold of 80%, the correlation between the quantity of $Sat_{O_2}$ limit threshold breaches and AUC is 93% with the AUC at 25 or more, and then falls off sharply thereafter. With a $Sat_{O_2}$ limit threshold of 90%, the correlation peaks at a much high value of AUC, and the correlation is much lower: a peak correlation of 0.66 with the AUC at 40 or more Analysis of the patient sample seems to show that the highest values of computed AUC tend to be correlated with $Sat_{O_2}$ threshold crossings of from 1-to-2 per hour. That is, $Sat_{O_2}$ threshold crossings of one or more in a given hour correspond to higher computed AUC.

Operationally, the implication of this is as follows: should a patient experience a number of breaches of the $Sat_{O_2}$ limit threshold, the AUC threshold limit can be increased to be greater than 25. Alternately, if the patient is experiencing fewer than 1 $Sat_{O_2}$ threshold breach per hour, the AUC threshold limit can be reduced to, for example, a value of 10.

Figure 5:
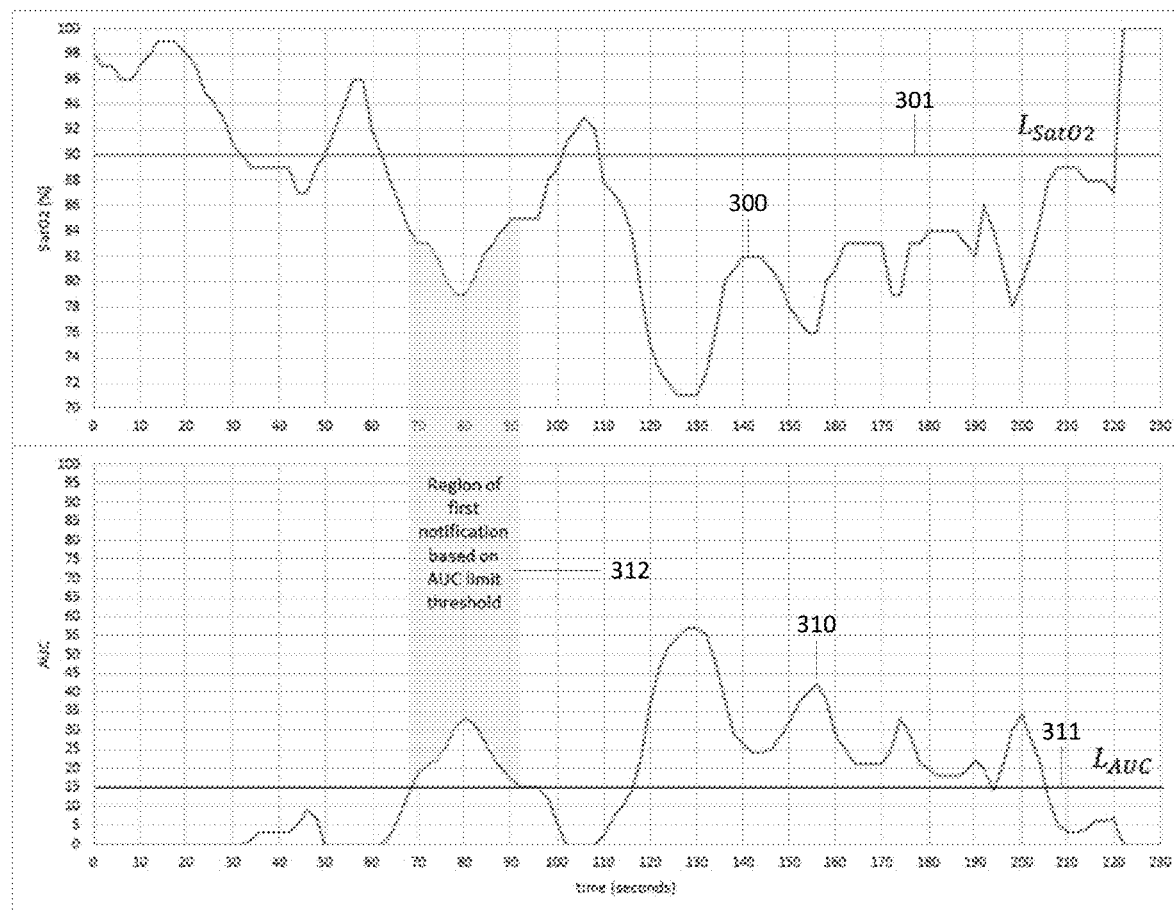
FIG. 5 illustrates time alignment of the AUC calculation with the $Sat_{O_2}$ time series.

FIG. 5 is a composite figure showing the oxygen saturation plot of FIG. 2 and the AUC plot of FIG. 4. FIG. 5, by aligning the measured arterial oxygen saturation values 300 with the AUC calculation 310, illustrates that in response to both the limit setting for AUC 311 as well as the arterial oxygen saturation limit setting 301, the regions or areas in which notifications or alarms are issued due to an AUC threshold breach 312 can be adjusted.

Figure 6:
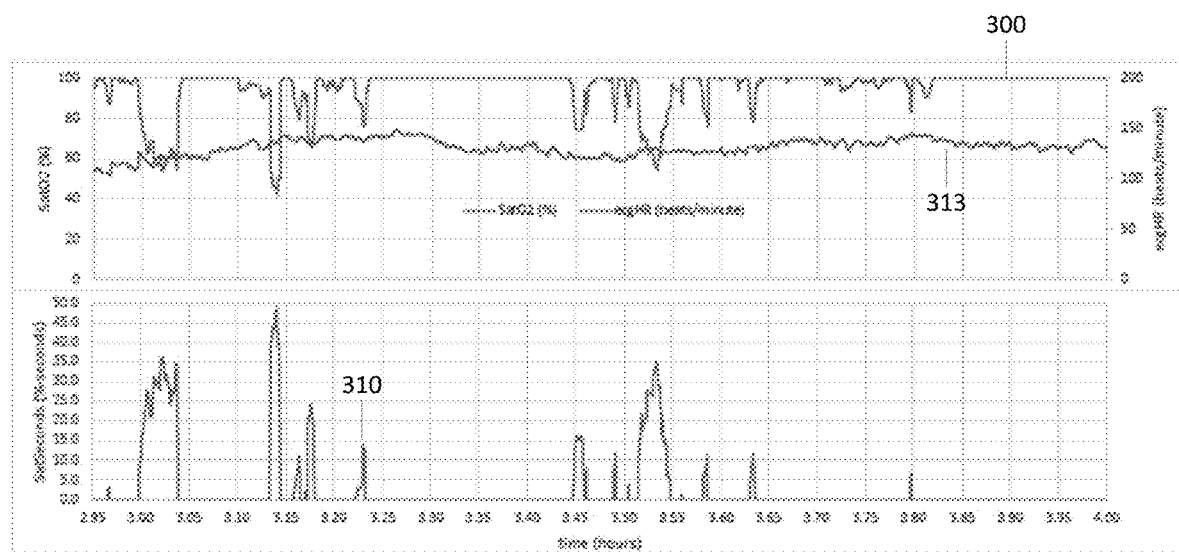
FIG. 6 depicts plots of the $Sat_{O_2}$, heart rate, HR, and AUC aligned versus time for a single patient monitored in an intensive care unit over a time span of 4 hours.

An actual example set of measurements to which the calculation has been applied is illustrated in FIG. 6. The lower plot of FIG. 6 is an AUC calculation over time 310 made by taking $O_2$ saturation measurements 300 of an intensive care unit patient over a span of 4 hours. The plot demonstrates the calculation of AUC relative to a $Sat_{O_2}$ limit threshold of 90%. Overlaid on the upper plot are the $Sat_{O_2}$ 300 and the heart rate 313 corresponding to this one patient.

Figure 7:
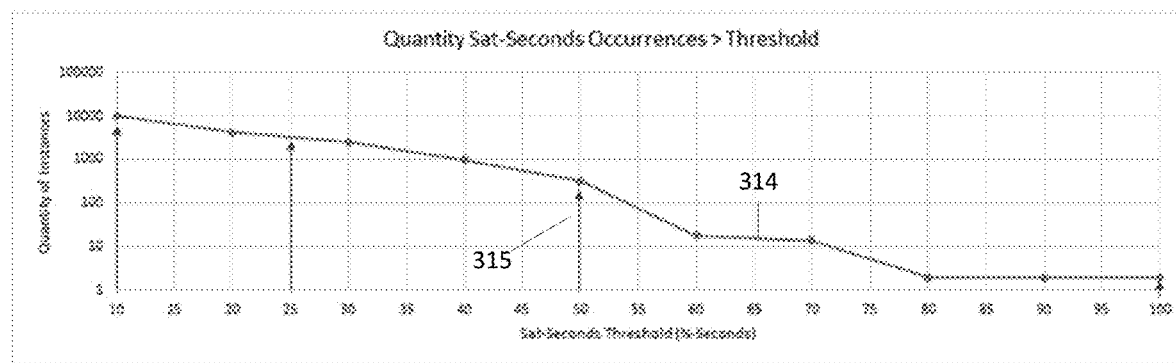
FIG. 7 plots the number of threshold breaches against AUC threshold based on a single 20-bed ICU comprising more than 965,000 measurements of $Sat_{O_2}$.

FIG. 7 plots the number of threshold breaches against AUC threshold. This plot was compiled using the measurement data compiled in a single 20-bed ICU comprising more than 965,000 measurements of $Sat_{O_2}$. Shown in the plot are the quantities of $Sat_{O_2}$ threshold breaches versus $L_{AUC}$ threshold 314. The red arrows 315 indicate the general limit thresholds of SatSeconds used by Medtronic pulse oximetry equipment and are overlaid for comparison to indicate the corresponding quantities of $Sat_{O_2}$ breaches relative to increasing the AUC threshold.

Figure 8:
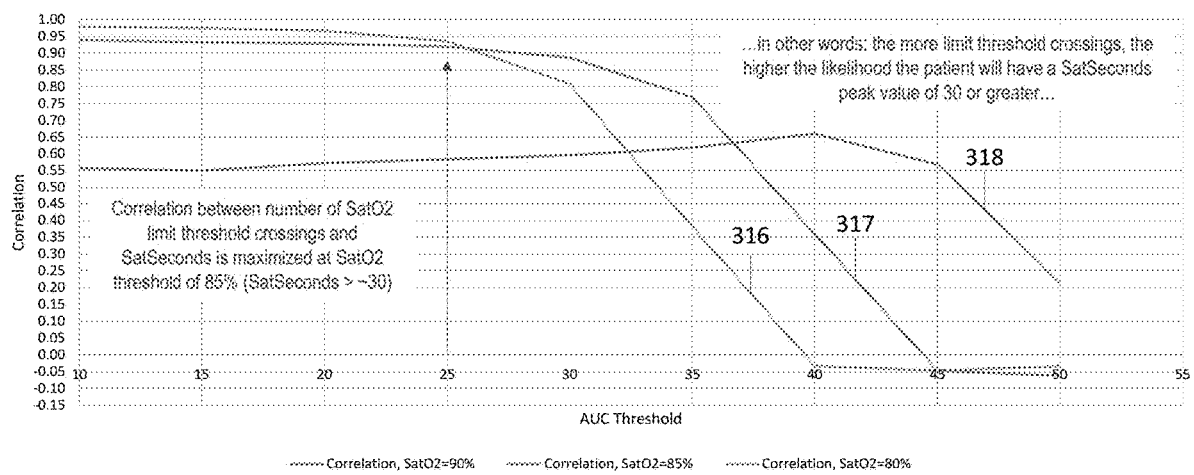
FIG. 8 plots the correlation between the likelihood of AUC being above a specific threshold parameterized against $Sat_{O_2}$ limit thresholds of 90%, 85%, and 80%.

As described in the paragraphs above, FIG. 8 plots the correlation between the likelihood of AUC being above a specific threshold parameterized against $Sat_{O_2}$ limit thresholds of 90%, 85%, and 80%. Thus, if the $Sat_{O_2}$ threshold was set to 80% 316, then this corresponded to a better-than 0.9 level of correlation that AUC would range above the value 25. If the $Sat_{O_2}$ threshold was set to 85% 317, then the likelihood that AUC would exceed 30 increased to a 0.9 level of correlation. If the $Sat_{O_2}$ threshold was set to 90% 318, then the correlation that AUC would exceed 30 peaks at AUC above 40, and the correlation is significantly less. A chief reason for this, as inferred from observations, is that the quantity of $Sat_{O_2}$ threshold crossings grows to such a great number that the AUC diminishes in value as a discriminant.

Figure 9:
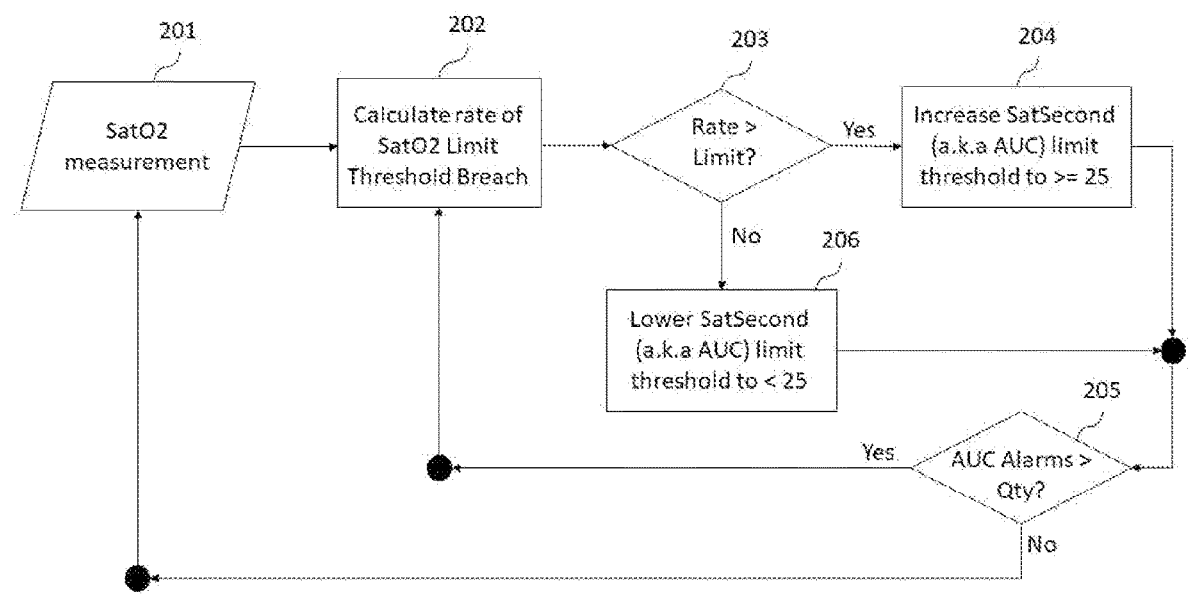
FIG. 9 is a flowchart of the method of adjusting the AUC threshold.

FIG. 9 is a flow diagram of a control algorithm for an embodiment of the invention. Oxygen Saturation measurements 201 are received from an oximeter at a specified acquisition rate by a processor or server. In one embodiment the acquisition rate is no fewer than once every 2 seconds. The processor or server evaluates the rate at which a limit threshold on $Sat_{O2}$ is breached 202 based on the incoming measurements for a particular patient. If the number of threshold breaches exceeds once per hour 203 then the saturation threshold limit ($L_{Auc}$) is increased 204 to 25 or above, otherwise, the limit threshold remains set below 25 206. If, after increasing the limit threshold on AUC, the frequency of $Sat_{O2}$ limit breaches continues to increase 205, then the $Sat_{O2}$ threshold is increased to a minimum of 50. This process continues until $Sat_{O2}$. AUC threshold is increased finally to a level of 100 (upper maximum).

This methodology is suggestive of an algorithm whereby all $Sat_{O_2}$ threshold breaches can be evaluated against the empirical limit frequency of one or more per hour: patients experiencing fewer than one per hour may be good candidates to consider adjusting the AUC limit to below 25. On most physiologic monitors so equipped with the calculation, the lowest value is 10. Selecting this value as a minimum threshold implies that any alarms associated with the AUC will still be issued from the medical device should a patient experience a threshold breach, but the quantities of alarms that are issued can be attenuated to a degree due to the adjustment made, which would be done on a per-patient basis Unless specifically stated otherwise as apparent from the following discussion, it is appreciated that throughout the description, discussions utilizing terms such as "processing" or "computing" or "calculating" or "delaying" or "comparing", "generating" or "determining" or "forwarding or "deferring" "committing" or "interrupting" or "handling" or "receiving" or "buffering" or "allocating" or "displaying" or "flagging" or Boolean logic or other set related operations or the like, refer to the action and processes of a computer system, or electronic device, that manipulates and transforms data represented as physical (electronic) quantities within the computer system's or electronic devices' registers and memories into other data similarly represented as physical quantities within electronic memories or registers or other such information storage, transmission or display devices.

The algorithms presented herein are not inherently related to any particular computer or other apparatus. Various general purpose systems may be used with programs in accordance with the teachings herein, or it may prove convenient to construct more specialized apparatus to perform the required method steps. The required structure for a variety of these systems will appear from the description below. In addition, the present invention is not described with reference to any particular programming language, and various embodiments may thus be implemented using a variety of programming languages.

A number of implementations have been described. Nevertheless, it will be understood that various modifications may be made without departing from the spirit and scope of the disclosure. For example, various forms of the flows shown above may be used, with steps re-ordered, added, or removed. Accordingly, other implementations are within the scope of the following claims.

The examples presented herein are intended to illustrate potential and specific implementations of the present disclosure. The examples are intended primarily for purposes of illustration of the invention for those skilled in the art. No particular aspect or aspects of the examples are necessarily intended to limit the scope of the present invention.

The figures and descriptions of the present invention have been simplified to illustrate elements that are relevant for a clear understanding of the present invention, while eliminating, for purposes of clarity, other elements. Those of ordinary skill in the art may recognize, however, that these sorts of focused discussions would not facilitate a better understanding of the present disclosure, and therefore, a more detailed description of such elements is not provided herein.

The processes associated with the present embodiments may be executed by programmable equipment, such as computers. Software or other sets of instructions that may be employed to cause programmable equipment to execute the processes may be stored in any storage device, such as, for example, a computer system (non-volatile) memory, an optical disk, magnetic tape, or magnetic disk. Furthermore, some of the processes may be programmed when the computer system is manufactured or via a computer-readable memory medium.

It can also be appreciated that certain process aspects described herein may be performed using instructions stored on a computer-readable memory medium or media that direct a computer or computer system to perform process steps. A computer-readable medium may include, for example, memory devices such as diskettes, compact discs of both read-only and read/write varieties, optical disk drives, and hard disk drives. A computer-readable medium may also include memory storage that may be physical, virtual, permanent, temporary, semi-permanent and/or semi-temporary.

Computer systems and computer-based devices disclosed herein may include memory for storing certain software applications used in obtaining, processing, and communicating information. It can be appreciated that such memory may be internal or external with respect to operation of the disclosed embodiments. The memory may also include any means for storing software, including a hard disk, an optical disk, floppy disk, ROM (read only memory), RAM (random access memory), PROM (programmable ROM), EEPROM (electrically erasable PROM) and/or other computer-readable memory media. In various embodiments, a "host," "engine," "loader," "filter," "platform," or "component" may include various computers or computer systems, or may include a reasonable combination of software, firmware, and/or hardware.

In various embodiments of the present disclosure, a single component may be replaced by multiple components, and multiple components may be replaced by a single component, to perform a given function or functions. Except where such substitution would not be operative to practice embodiments of the present disclosure, such substitution is within the scope of the present disclosure. Any of the servers, for example, may be replaced by a "server farm" or other grouping of networked servers (e.g., a group of server blades) that are located and configured for cooperative functions. It can be appreciated that a server farm may serve to distribute workload between/among individual components of the farm and may expedite computing processes by harnessing the collective and cooperative power of multiple servers. Such server farms may employ load-balancing software that accomplishes tasks such as, for example, tracking demand for processing power from different machines, prioritizing and scheduling tasks based on network demand, and/or providing backup contingency in the event of component failure or reduction in operability.

In general, it may be apparent to one of ordinary skill in the art that various embodiments described herein, or components or parts thereof, may be implemented in many different embodiments of software, firmware, and/or hardware, or modules thereof. The software code or specialized control hardware used to implement some of the present embodiments is not limiting of the present disclosure. Programming languages for computer software and other computer-implemented instructions may be translated into machine language by a compiler or an assembler before execution and/or may be translated directly at run time by an interpreter.

Examples of assembly languages include ARM, MIPS, and x86; examples of high level languages include Ada, BASIC, C, C++, C#, COBOL, Fortran, Java, Lisp, Pascal, Object Pascal; and examples of scripting languages include Bourne script, JavaScript, Python, Ruby, PHP, and Perl. Various embodiments may be employed in a Lotus Notes environment, for example. Such software may be stored on any type of suitable computer-readable medium or media such as, for example, a magnetic or optical storage medium. Thus, the operation and behavior of the embodiments are described without specific reference to the actual software code or specialized hardware components. The absence of such specific references is feasible because it is clearly understood that artisans of ordinary skill would be able to design software and control hardware to implement the embodiments of the present disclosure based on the description herein with only a reasonable effort and without undue experimentation.

Various embodiments of the systems and methods described herein may employ one or more electronic computer networks to promote communication among different components, transfer data, or to share resources and information. Such computer networks can be classified according to the hardware and software technology that is used to interconnect the devices in the network.

The computer network may be characterized based on functional relationships among the elements or components of the network, such as active networking, client-server, or peer-to-peer functional architecture. The computer network may be classified according to network topology, such as bus network, star network, ring network, mesh network, star-bus network, or hierarchical topology network, for example. The computer network may also be classified based on the method employed for data communication, such as digital and analog networks.

Embodiments of the methods, systems, and tools described herein may employ internetworking for connecting two or more distinct electronic computer networks or network segments through a common routing technology. The type of internetwork employed may depend on administration and/or participation in the internetwork. Non-limiting examples of internetworks include intranet, extranet, and Internet. Intranets and extranets may or may not have connections to the Internet. If connected to the Internet, the intranet or extranet may be protected with appropriate authentication technology or other security measures. As applied herein, an intranet can be a group of networks which employ Internet Protocol, web browsers and/or file transfer applications, under common control by an administrative entity. Such an administrative entity could restrict access to the intranet to only authorized users, for example, or another internal network of an organization or commercial entity.

Unless otherwise indicated, all numbers expressing lengths, widths, depths, or other dimensions and so forth used in the specification and claims are to be understood in all instances as indicating both the exact values as shown and as being modified by the term "about." As used herein, the term "about" refers to a ±10% variation from the nominal value. Accordingly, unless indicated to the contrary, the numerical parameters set forth in the specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques. Any specific value may vary by 20%.

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are intended to be embraced therein.

It will be appreciated by those skilled in the art that various modifications and changes may be made without departing from the scope of the described technology. Such modifications and changes are intended to fall within the scope of the embodiments that are described. It will also be appreciated by those of skill in the art that features included in one embodiment are interchangeable with other embodiments; and that one or more features from a depicted embodiment can be included with other depicted embodiments in any combination. For example, any of the various components described herein and/or depicted in the figures may be combined, interchanged, or excluded from other embodiments.

What is claimed is:

1. A method for adjusting a current area under the curve (AUC) limit threshold to reduce a number of false alarms by calculating a number of times a blood oxygen saturation signal breaches the current limit threshold, comprising the steps of:

defining a AUC limit threshold in response to a blood oxygen saturation signal received from a patient blood oxygen saturation monitor;

defining a blood oxygen saturation limit threshold for a desired blood oxygen saturation level;

measuring a patient's measured blood oxygen saturation level over time;

calculating the difference between the patient's measured blood oxygen saturation and the defined blood saturation limit threshold;

summing the differences between the patient's measured blood oxygen saturation and a defined blood oxygen saturation limit threshold over a time interval wherein the patient's measured blood oxygen saturation is less than defined blood oxygen saturation limit threshold, wherein the summation defines a measured AUC;

comparing the measured AUC over the time interval against the defined AUC limit threshold;

determining regions in which the measured AUC exceeds the defined AUC limit threshold;

calculating a quantity of occurrences in which the AUC exceeds the defined AUC limit threshold to determine a frequency of occurrence of threshold crossings;

responsive to determining that the frequency of occurrence of threshold crossings exceeds one occurrence per hour, adjusting the AUC limit threshold to at least a value of 25; and responsive to determining that the frequency of occurrence of threshold crossings equals or falls below one occurrence per hour, adjusting the AUC limit threshold below a value of 25.

2. The method in claim 1, wherein the AUC limit threshold is configured by a clinician.

3. The method in claim 1, wherein the AUC limit threshold is configured based on historical data from the patient, a given medical unit associated with the patient, or a given demographic.

4. The method in claim 1, wherein the blood oxygen saturation limit threshold is configured by a clinician.

5. The method in claim 1, wherein the blood oxygen saturation limit threshold is configured based on historical data from the patient, a given medical unit associated with the patient, or a given demographic.

6. The method in claim 1, wherein the blood oxygen saturation limit threshold comprises an upper limit threshold and a lower limit threshold.

7. The method in claim 6, wherein an alarm threshold is determined for one of a number of physiologic and clinical measurements, wherein the number of physiologic and clinic measures includes at least one of one or more heart rates, one or more respiratory rates, one or more blood pressures, one or more infusions, and one or more flows of bodily fluids.

8. A system for adjusting a current area under the curve (AUC) limit threshold to reduce a number of false alarms by calculating a number of times a blood oxygen saturation signal breaches the current limit threshold comprising:

a user interface to configure a saturation limit threshold for a patient's oxygen saturation level and AUC limit threshold in response to a blood oxygen saturation signal received from a patient blood oxygen saturation monitor, wherein an alarm system operatively coupled to the user interface is configured to emit an alarm when the patient's oxygen saturation level is below the oxygen saturation limit threshold;

a blood oxygenation saturation sensor to measure a patient's blood oxygen saturation level over time; and a processor in communication with the blood oxygenation saturation sensor and configured to:
  calculate the difference between a patient's measured blood oxygen saturation and a defined blood saturation limit threshold;
  sum the differences between the patient's measured blood oxygen saturation and the defined blood oxygen saturation limit threshold over a time interval wherein the patient's measured blood oxygen saturation is less than defined blood oxygen saturation limit threshold, wherein the summation defines a measured AUC;
  compare the measured AUC over the time interval against the AUC limit threshold;
  determine regions in which the measured AUC exceeds the defined AUC limit threshold; and
  calculate a quantity of occurrences in which the AUC exceeds the defined AUC limit threshold to determine a frequency of occurrence of threshold crossings;
  responsive to determining that the frequency of occurrence of threshold crossings exceeds one occurrence per hour, adjust the AUC limit threshold to at least a value of 25; and
  responsive to determining that the frequency of occurrence of threshold crossings equals or falls below one occurrence per hour, adjust the AUC limit threshold below a value of 25.

* * * * *